(12) United States Patent
Hunter et al.

(10) Patent No.: US 7,479,101 B2
(45) Date of Patent: Jan. 20, 2009

(54) METHOD FOR TREATING AN ANIMAL USING A CONSTANT AMPLITUDE ELECTROMAGNETIC FIELD

(75) Inventors: Clifford Wayne Hunter, Houston, TX (US); Robert Emmett Ward, Jr., Houston, TX (US); Donald Coolidge Wunsch, Albuquerque, NM (US)

(73) Assignee: KSM, Inc., Bellaire, TX (US)

( * ) Notice: Subject to any disclaimer, the term of this patent is extended or adjusted under 35 U.S.C. 154(b) by 166 days.

(21) Appl. No.: 11/558,876

(22) Filed: Nov. 10, 2006

(65) Prior Publication Data
US 2007/0260291 A1    Nov. 8, 2007

Related U.S. Application Data

(63) Continuation-in-part of application No. 11/408,408, filed on Apr. 21, 2006.

(60) Provisional application No. 60/673,398, filed on Apr. 21, 2005.

(51) Int. Cl.
*A61N 1/00* (2006.01)

(52) U.S. Cl. .......................................... 600/13

(58) Field of Classification Search ................ 600/9–15
See application file for complete search history.

(56) References Cited

U.S. PATENT DOCUMENTS

| | | | |
|---|---|---|---|
| 4,066,065 A | 1/1978 | Kraus | |
| 4,738,797 A * | 4/1988 | Halpern et al. | 508/508 |
| 4,993,413 A | 2/1991 | McLeod et al. | |
| 6,042,531 A * | 3/2000 | Holcomb | 600/13 |
| 6,290,638 B1 | 9/2001 | Canedo et al. | |
| 6,641,520 B2 | 11/2003 | Bailey et al. | |
| 2002/0103411 A1 | 8/2002 | Bailey et al. | |

FOREIGN PATENT DOCUMENTS

| | | |
|---|---|---|
| GB | 2217990 A | 11/1989 |
| WO | 0126805 A1 | 5/1984 |
| WO | 2007044386 | 4/2007 |

\* cited by examiner

*Primary Examiner*—Samuel G Gilbert
(74) *Attorney, Agent, or Firm*—Buskop Law Group, PC; Wendy Buskop

(57) ABSTRACT

A method for treating an animal using a constant amplitude electromagnetic field including: providing at least one constant amplitude electromagnetic field focused at a center location, continuously maintaining an area around the constant amplitude electromagnetic field at a constant temperature, placing an end of a limb of an animal at the center location, exposing the end of the limb of the animal to the constant amplitude electromagnetic field for a length of time ranging from 10 minutes to 3 hours to simultaneously treat venous and arterial blood cells and nerve endings in the limb of the animal.

20 Claims, 6 Drawing Sheets

METHOD FOR TREATING AN ANIMAL USING A CONSTANT AMPLITUDE ELECTROMAGNETIC FIELD

CROSS-REFERENCE TO RELATED APPLICATIONS

This patent application is a continuation-in-part application that claims the benefit, under 35 USC §120, of the prior non-provisional application Ser. No. 11/408,408, which was filed Apr. 21, 2006 pending; which claimed priority to a provisional application 60/673,398, which was filed on Apr. 21, 2005. The prior co-pending non-provisional application and prior provisional application are incorporated by reference along with their appendices.

FIELD

The present embodiments relate generally to a method for treating an end of an limb of an animal using a constant amplitude electromagnetic field.

BACKGROUND

The invention will be described with reference to the drawings, the detailed description, and the appended claims.

There exists a need for a method capable of treating acute pain in an animal or human with a constant amplitude electromagnetic field.

There exists a need for a method for applying a constant amplitude electromagnetic field that is capable of treating an animal or human in a consistent repeatable manner, regardless of the training of the operator.

There exists a need for a method for applying a constant amplitude electromagnetic field that has a switchable continuous flow cooling system, such that all magnetic modules are maintained at a temperature less than 105 Degrees.

The present embodiments meet these needs.

BRIEF DESCRIPTION OF THE DRAWINGS

The detailed description will be better understood in conjunction with the accompanying drawings as follows.

Figure 1:
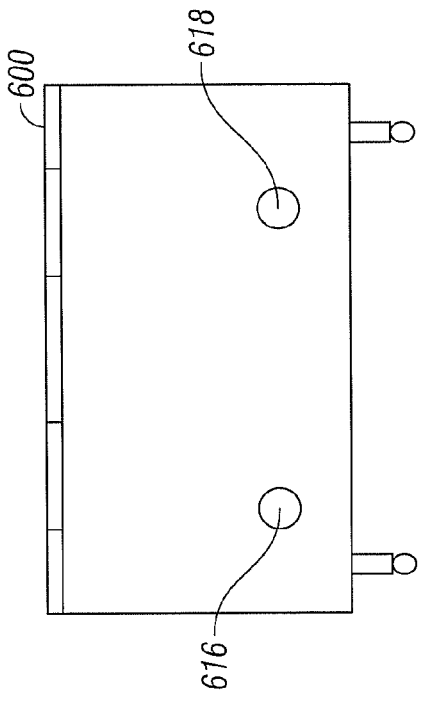
FIG. 1 is a left and right view of an embodiment of the housing without the magnetic modules.
Figure 1:
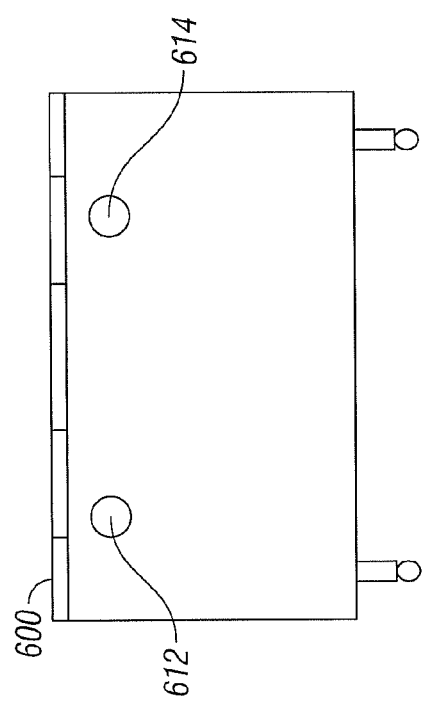

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The invention relates to a method for treating an animal using a constant amplitude electromagnetic treatment system. Particularly, the constant amplitude electromagnetic treatment system provides a constant amplitude electromagnetic field.

The current method selectively includes exposing an end of an limb of an animal to the constant amplitude electromagnetic field for a predetermined length of time. For the results of the treatment to be observed the predetermined length of time can range from approximately 10 minutes to 3 hours.

It is contemplated that an embodiment of the method could provide from 2 to 4 constant amplitude electromagnetic fields with each of the constant amplitude electromagnetic fields being adapted to treat the end of the limb of an animal.

The constant amplitude electromagnetic field can have an intensity from 50 to 1000 gauss at a center location where treatment occurs. The intensity of the constant amplitude electromagnetic field declines in intensity as the distance from the center location increases. The electromagnetic field can decline from up to 80% to 90% of its original intensity at a location approximately 2 feet from the center location.

The constant amplitude electromagnetic field has constant directional vector electromagnetic gradients inward and outward from the treatment volume. The constant amplitude electromagnetic field is concentrated at the center location.

During the exposure, the constant amplitude electromagnetic field simultaneously treats venous and arterial blood cells as well as nerve endings in the limb of the animal. Once the treatment is provided for a length of time ranging from 10 minutes to about 3 hours, the exposure of the end of the limb of the animal is stopped. The exposure is stopped by removing the end of the limb from the center location.

The method for providing constant amplitude electromagnetic treatment can include using a continuous flow cooling system, which continuously maintains a temperature of less than 105 degrees Fahrenheit within an area around the constant amplitude electromagnetic field. The temperature can be continuously maintained using a cooling fluid.

The continuous flow cooling system can further include periodically removing heat from the cooling fluid to the external environment.

In an alternative embodiment, the cooling fluid can be a hydrotreated light naphthenic petroleum oil. The cooling fluid, in the continuous flow cooling system is used to maintain the temperature within the magnetic module at an appropriate level. The appropriate level can range from the ambient temperature to less than 105 degrees Fahrenheit. The ambient temperature should range from 68 degrees Fahrenheit to 80 degrees Fahrenheit.

In another alternative, non-limiting embodiment of the method, the constant amplitude electromagnetic field can be automatically stopped when the temperature in the area around the constant amplitude electromagnetic field exceeds a pre-set limit.

It is additionally contemplated that when multiple constant amplitude electromagnetic fields are used, one field can be off while others are in use.

It is contemplated that each constant amplitude electromagnetic field can be adapted to treat limbs of different animals simultaneously.

In an alternative embodiment, it is contemplated that the animal can be a human.

In addition to a method for treating an animal, the invention relates to a constant amplitude electromagnetic system for treating an end of a limb of an animal. A non-limiting embodiment of the constant amplitude electromagnetic treatment system typically contains four wound magnetic wire coils each with an opening (or aperture) at its center that allows a body part or appendage, i.e., a hand, arm, foot, or leg, to be suitably positioned to efficiently be exposed to a continuous DC constant amplitude electromagnetic field.

Features of an embodiment of a constant amplitude electromagnetic treatment system include, but are not limited to safety locked controls; an integrated continuous flow cooling system; the use of static electromagnetic fields, which produce minimal extraneous electromagnetic fields; non-invasive patient treatment; simple non-adjustable on-off controls; operation status metering for each magnetic module; operation of standard 220 volt wall power, electrical safety tested, and wheel mounted, or in the alternative the wall power can be can be 230 volt AC, 20 amperes, 50 Hz.

The Provisional Application, incorporated by reference in its entirety, provides additional examples in the form of photographs and schematics related to the present invention.

In certain embodiments of the invention, described below and in the figures, a system can be approximately 6½'×2½'×4' high and weigh in excess of 2000 pounds. The system can contain four wound magnetic wire coils with central openings of 4.25", 4.25", 6.25", and 8.25" diameters and in certain embodiments approximately 4" in length. The system can be powered by single phase, 220 volt AC. The AC can be rectified to approximately 220 volt DC by separate full-wave bridge rectifier circuitry to each wound magnetic wire coil. AC power can be supplied to a pump and fan, providing circulation of dielectric oil to each wound magnetic wire coil. The system can be connected by a 220-volt, 20 ampere, three wire, grounded, UL approved power cable. In operation each wound magnetic wire coil draws approximately 2.3 amperes, and the system with all systems operating draws approximately 17 amperes. AC power switches can be separately provided for main power, each wound magnetic wire coil, the pump, and the fan. The wound magnetic wire coils can be surrounded, with the exception of the aperture, by a closed ferromagnetic housing. Other alternative materials can be used but are not as good. Such materials could include stainless steel, aluminum, or titanium. The ferromagnetic housing can be filled with dielectric oil for additional insulation and cooling. All wound magnetic wire coils, the pump, the fan, and the power circuitry housings can be solidly electrically grounded to the metal structural housing.

The housing can be electrically connected to the ground wire of the power cable. All operating features are typically completely controlled by on-off switches. Computer microprocessor or software systems need not be employed. The main electrical function is to provide DC Current to the wound magnetic wire coils. All circuitry is of standard design and implemented with proven robust conservatively rated components.

The constant amplitude electromagnetic system can have a lockable front cover. There are several contemplated controls and meters for operating the constant amplitude electromagnetic field system.

All controls can be located behind a hinged lockable front panel. During operation it is contemplated that the panel remain unlocked for quick access to all controls.

The system controls are typically simple on-off switches, however it is contemplated that variable types of switches can be used. There is no apparent need for variable or adjustable controls. There may be various types of switches including one or more switches separately controlling the power to a wound magnetic wire coil. Each switch should be clearly labeled to indicate the magnetic module it controls; at least one second switch can control the continuous flow cooling system, and a third switch can control the cooling fan for the heat exchanger. It is advisable that when a magnetic module is on, both the fan and pump are also on.

Adjacent to each switch is an ammeter that indicates the current being drawn to the load controlled by that switch. Each ammeter can also be separately labeled with the same number as to its related switch and load. The meters can be physically located so that they cannot be easily confused. The meters for the switches to the left can be located to the left of the corresponding switches, and the meters for the switches to the right can be located to the right of the corresponding switches. The meters may all be identical to avoid confusion. They read to a maximum of 10 amperes of AC current with subdivisions of 2 amperes. The four meters that indicate the power to the magnetic coils measure the AC currents being supplied before rectification. The pump and fan ammeters measure the AC current drawn by the respective units. A temperature monitoring system, such as a thermometer, may also be installed in or around an aperture or the magnetic wire coil to measure the temperature at each magnetic module.

The system may be powered by 220 volt AC, 20 amperes, 60 Hz. In another, non-limiting alternative embodiment, the system can be powered using 230 volt AC, 20 amperes, 50 Hz. Main power switches may include, but are not limited to individual on-off switches for each operating magnetic module, the pump, and the fan. There may also be provided a locked key access to control panel or some other mechanism to regulate access to the controls.

The system may further comprise dielectric insulation including insulation with wide safety margins, particularly between active coils and an animal or human. The insulation may include wiring dielectric interfaces and dielectric insulation oil. The oil may also serve as a coolant. A patient's arm or leg may rest within a dielectric cuff.

Figure 4:
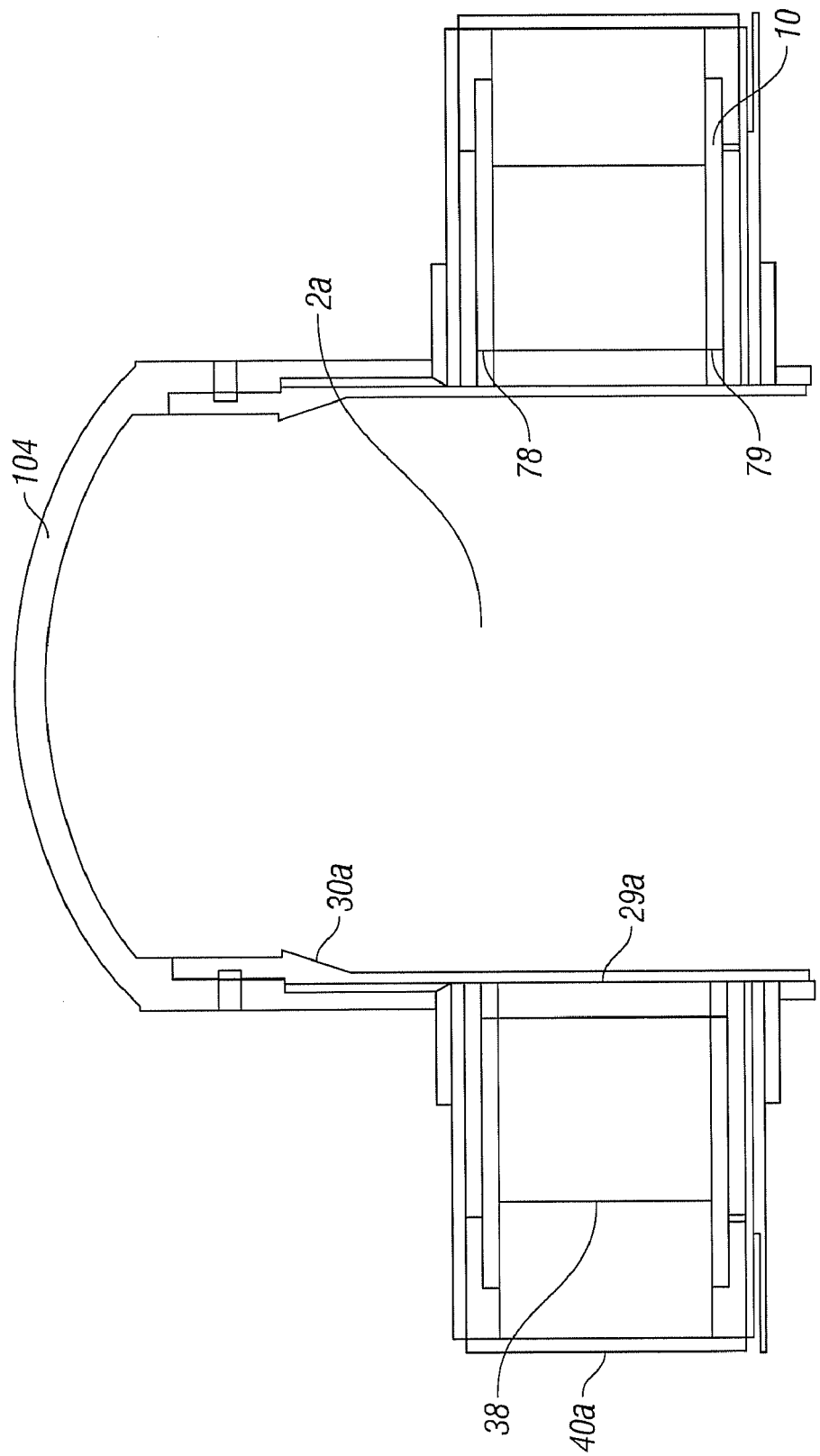
FIG. 4 is a depiction of an embodiment of a magnetic module.

Typically, AC current will be rectified to DC current before powering the magnetic modules. The AC power is typically connected to full-wave bridge rectifier circuit(s) that provide the DC voltage to the magnetic coil(s) through control switches. An exemplary electrical schematic is illustrated in FIG. 4.

The constant amplitude electromagnetic system exposes an end of a limb of an animal selective disposed within an aperture to a DC constant amplitude electromagnetic field. For safety considerations, the magnitude of this field can be compared to the magnetic fields approved for use in Magnetic Resonance Imaging (MRI) and Magnetic Resonance Spectroscopy (MRS) diagnostic systems. The magnetic fields in such systems can expose the whole patient body to levels up to 100,000 gauss. The constant amplitude electromagnetic system exposes only extremities of the patient to levels significantly below those of a typical MRI system. The wound magnetic wire coil, being a solenoid and being powered by direct current, produces a electromagnetic field which rapidly decreases in intensity within short distances from the end of the wound magnetic wire coil.

The constant amplitude electromagnetic system includes several mechanical features. The switchiable continuous flow cooling system uses a pump to force cooling fluid into each of the magnetic modules. A non-limiting example of a coolant circulation pump is a Model TE-6MD-SC-c-csa 586504 (Little Giant Pump Company). The Pump can be powered by a ½ hp motor with electrical requirements of 230 volts, 60 Hz, 4.5 amps. All electrical power is provided with hard wire direct connections internal to the constant amplitude electromagnetic system. The power to the pump may be controlled by a control switch on the system control panel.

The switchable continuous flow cooling system also uses a fan as part of the heat exchanger. An exemplary cooling fan is manufactured by Thermal Transfer Products LTD. The power to the fan may be controlled by a control switch on a system control panel.

An exemplary heat exchanger is manufactured by thermal Transfer Products LTD.

The constant amplitude electromagnetic system may be operated in the following way. The system's power cable may be connected to a standard GFI wall outlet rated at 220-volt and 30 amperes. It is advisable that the outlet be fed from a 220-volt, single phase, minimum 20-amperes source fused or over current breaker rated for 20 amperes. The room air conditioning system should be capable of maintaining an ambient temperature from 68 degrees Fahrenheit to 80 degrees Fahrenheit, which optimizes the capabilities of the switchable continuous flow cooling system and provides for the animal's or human's comfort.

Once the system is plugged into an appropriate electrical outlet. The operator should first switch on the switchable continuous flow cooling system, then the operator should turn on the magnetic modules separately. The operator should monitor temperature gauges and check that the temperature does not exceed prescribed limits, such as 10 percent of the ambient temperature.

The switchable continuous flow cooling system should be engaged prior to the system being operated for any substantial length of time. The switchable continuous flow cooling system is designed to provide for removal of heat generated when the wound magnetic wire coils generate the constant amplitude electromagnetic field.

The non-flowing cooling fluid within each ferromagnetic housing will cool the wound magnetic wire coils for a substantial length of time. However, an operator should not allow the magnetic modules to be turned on for a significant period of time without turning on the switchable continuous flow cooling system.

The operator, when operating the constant amplitude electromagnetic system, should ensure the safety of the constant amplitude electromagnetic system at all times.

Exemplary safety measures include electrical safety tests using a QuadTech, Model Guardian 6100, Medical Production Safety Analyzer with current calibration certification. Safety test measurements that can be made include to (1) Ground Continuity, (2) Ground Bonding, (3) AC Hipot, (4) DC Hipot, (5) AC insulation resistance, (6) DC Insulation Resistance, and (7) Line Leakage Current.

In addition the operator should always ensure that constant amplitude electromagnetic treatment system is maintained to operate as designed. This means the operator should ensure that the constant amplitude electromagnetic treatment system should always meet curtain standards including the following: International Medical System Directives, ISO 60601-1, ISO 60601-1-1, 60601-1-2; medical functional and safety standards, ISO 14971; system risk analysis; and ISO 9000/ISO 13485 Quality Assurance Standards. These standards as referenced are the current 2006 standards. This ensures that each constant amplitude electromagnetic treatment system operates substantially similar and provides identical treatment conditions.

In the event that the constant amplitude electromagnetic system of the invention has not been used for an extended period of time, it should be prepared and stored in an appropriate manner.

This includes at a minimum: (a) ensuring the control panel is key locked and that the key is not left accessible with the system, (b) ensuring that the power cable is coiled and attached to the system in a manner such that it will not come free, drag on the floor, or drag within the wheel area of the system, (c) ensuring the cable and connector cannot be bent or crushed due to the placement of the system for storage, (d) covering the system or system completely in a manner to prevent dust or water from reasonably coming into contact with the system, and (e) storing the system in a temperature controlled environment or in an area in which the temperature remains in the range from 40 degrees Fahrenheit to 120 degrees Fahrenheit.

In another alternative embodiment of the constant amplitude electromagnetic system, the constant amplitude electromagnetic system has a ferromagnetic housing having at least one magnetic module. Each of the magnetic modules can have an aperture which is sized to receive at least one limb.

The constant amplitude electromagnetic system can further include a non-ferromagnetic segment forming each aperture. Furthermore, a tubular sleeve can be disposed within an aperture. The inner diameter of the tubular sleeve can have a diameter that ranges from 3 to 10 inches. It is further contemplated that the tubular sleeve can have an end cap.

The magnetic modules include a wound magnetic wire coil operatively connected to a perforated spindle. The wound magnetic wire coil has a coil diameter, which is greater than the magnetic wire coil's coil depth. The magnetic wire coil can surround each aperture.

It is also contemplated, that the magnetic wire coil can be contained between the non-ferromagnetic segment and the ferromagnetic housing.

The wound magnetic wire coil generates a constant amplitude electromagnetic field within the aperture when coupled to a direct electrical current. The constant amplitude electromagnetic field can be concentrated within the aperture.

In addition, the system includes a switchable continuous flow cooling system. It is contemplated that the switchable continuous flow coiling system simultaneously cools each wound magnetic wire coil within the ferromagnetic housing.

The switchable continuous flow cooling system can have a first cooling fluid reservoir. The first cooling fluid reservoir can be in fluid communication with a pump. The cooling fluid flows from the first cooling fluid reservoir to a pressurizable cooling fluid reservoir. The cooling fluid will flow from the pressurizable cooling fluid reservoir to each wound magnetic wire coil.

The cooling fluid flows around each of the wound magnetic wire coils, cooling the wound magnetic wire coils. The cooling fluid is used to maintain a substantially similar temperature in each of the magnetic modules. The temperature can range from ambient temperature to 105 degrees Fahrenheit. The cooling fluid will flow from the ferromagnetic housing to a heat exchanger. The heat exchanger can transfer heat from the cooling fluid to the outside environment. It is additionally contemplated, that the heat exchanger can be a fin, fan heat exchanger. After passing through the heat exchanger, the fluid can return to the first cooling fluid reservoir.

Each perforated spindle of the wound magnetic wire coils can have a plurality of elliptical openings. The openings allow the cooling fluid to surround the wound magnetic wire coil, thereby providing continuous convection cooling. It is contemplated that the cooling fluid can be a dielectric cooling fluid, such as a hydrotreated light naphthenic petroleum oil.

A plurality of spacers can separate the perforated spindle from the non-ferromagnetic segment.

It is contemplated that the pump, which pressurizes the cooling fluid in the presurizable reservoir, can be a switchable magnetic coupling fluid circulation pump. It is contemplated that the pump will not generate more than 20 psi of pressure.

The system can further include a plurality of switches to individually couple electrical current to each magnetic module.

It is contemplated that the tubular sleeve can be formed of an insulating material. The insulating material can be PVC, a non-toxic hard crystalline polymer, polyethylene, polypropylene, polyamide, a homopolymer of one of these polymers, a copolymer of one of these polymers, or combinations thereof.

The constant amplitude electromagnetic field is generally a static field but can contain a small amount of a dynamic magnetic field. The dynamic magnetic field can be from 3% to 5% of the constant amplitude electromagnetic field.

The constant amplitude electromagnetic field system can also have a power line filter connected to a power input for supplying electric current to the magnetic modules. In addition, a surge arrestor can be selectively located at the power input to ensure even transmission of the electrical current to the wound magnetic wire coils.

In an alternative, non-limiting embodiment, the system can include a fail safe circuitry. The fail safe circuitry can be adapted to prevent power from connecting to the wound magnetic wire coil when the temperature around the wound magnetic wire coil exceeds a preset limit.

The system can be best understood with reference to the Figures. Referring now to the Figures.

FIG. 1 is a prospective view of a non-limiting embodiment of the system. The left and right view of the housing 600 is depicted without the magnetic modules 12, 14, 16, and 18. The housing 600 has at least two holes 612 and 614 selectively disposed within the left side of housing 600. The housing 600 further has at least two more holes 616 and 618 selectively disposed within the right side of the housing 600.

The housing 600 can have a plurality of holes located at selective different positions. For example the housing can contain 4 holes with each hole having a different diameter for accommodating magnetic modules with varying sizes of apertures for receiving varying sizes of ends of limbs of the animal.

In addition, the holes can be located on the housing 600 in different alignments. For example, two modules can be aligned vertically perpendicular to each other so that the animal or person can insert a foot in one hole and a hand in another hole.

Another possible arrangement of the holes on the housing 600 can include two holes selectively placed so that the constant amplitude electromagnetic system can be positioned in a corner of a room, while still allowing access to the holes.

Another possible arrangement of the holes on the housing 600 can include two holes located on the left side of the housing 600, and two holes located on the right side of the housing 600. The holes on the left side of housing 600 can each be selectively located and sized to accommodate magnetic modules with apertures sized to receive a hand of a human. The holes on the left side of the housing 600 can each be selectively aligned and sized to accommodate magnetic modules with apertures sized to receive the feet of a human.

It is clear that there are several other possible arrangements of the holes and sizing of the holes located on the housing 600. The arrangements of the holes on the housing will be dictated by what is required by the specific use of the constant amplitude electromagnetic system.

Figure 2:
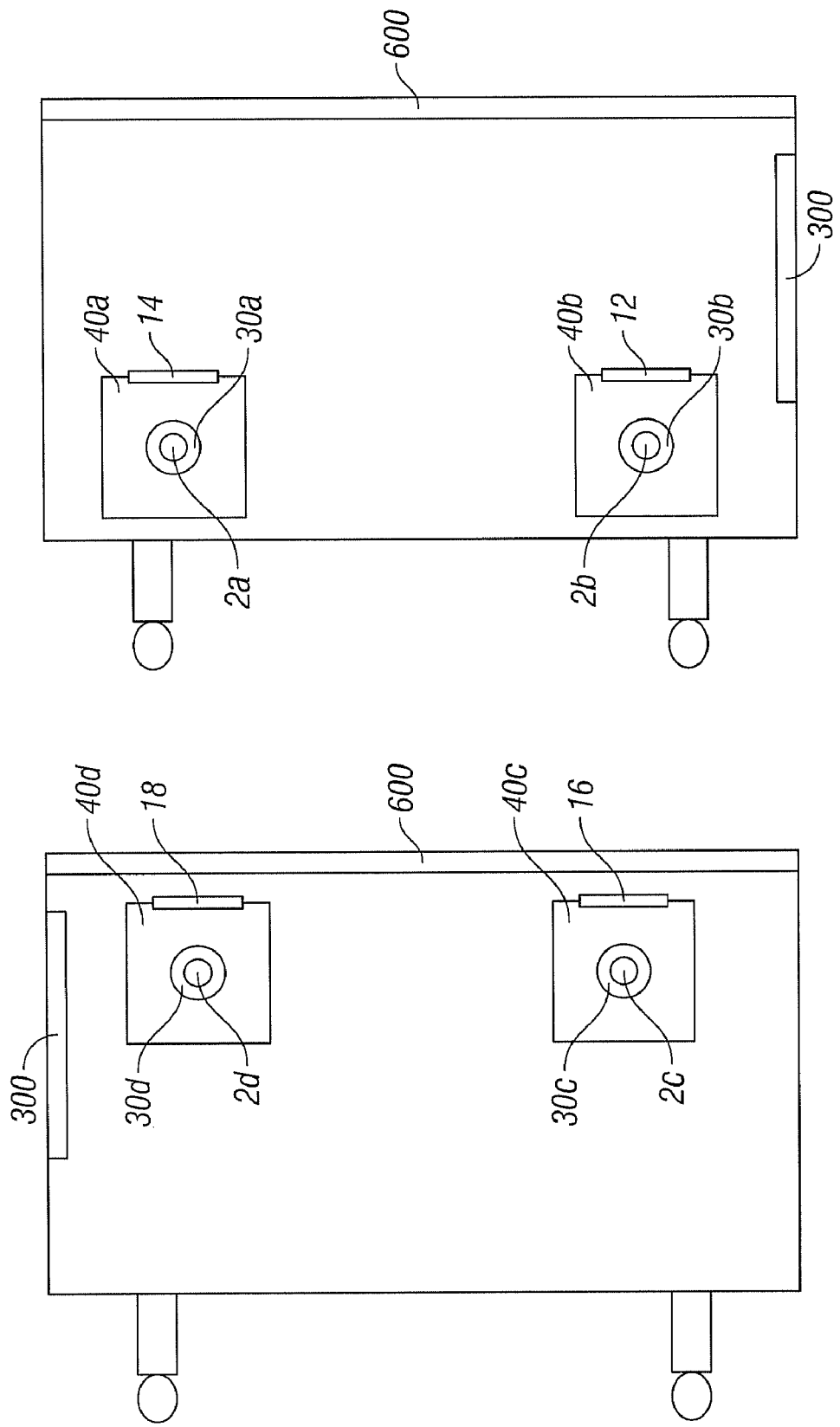
FIG. 2 depicts an embodiment of a left and right view of the housing with the magnetic modules.

Referring now to FIG. 2, the holes 612, 614, 616, and 618 are operatively and selectively disposed upon the housing 600 to align with the magnetic modules 12, 14, 16, 18.

Figure 3:
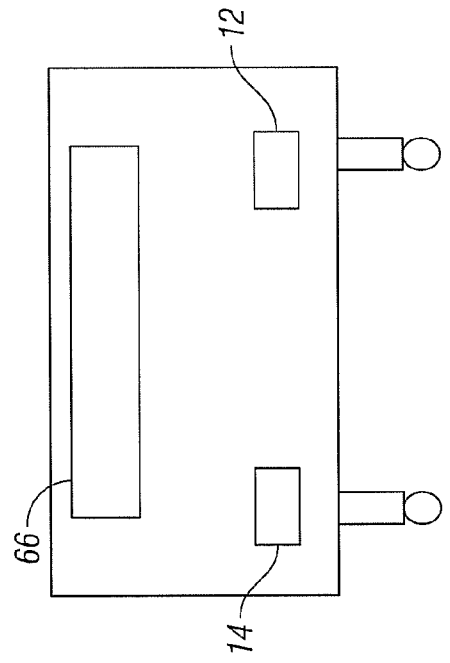
FIG. 3 depicts a left and right view of the inside of the housing.
Figure 3:
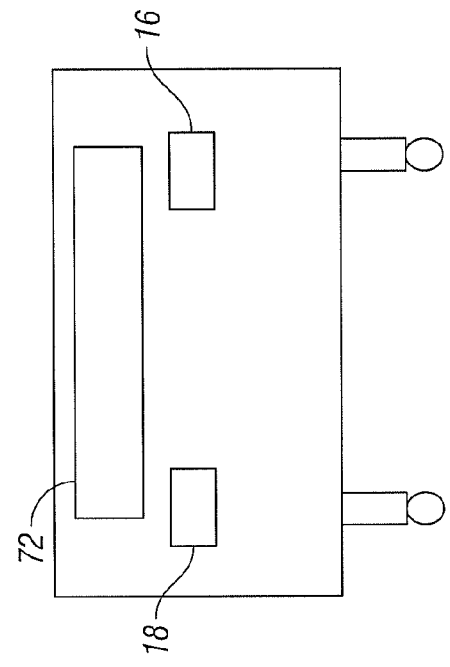

Referring now to FIG. 3, a first cooling reservoir 66 and a presurizable cooling reservoir 72 are selectively disposed within housing 600. The first cooling reservoir 66 is selectively aligned to the left of the pressurizable cooling reservoir 72. The first cooling reservoir 66 and the pressurizable cooling reservoir 72 are operatively positioned at a similar elevation within the housing 600. In the embodiment depicted in FIG. 3 the pressurizable reservoir 72 and first cooling reservoir 66 are in an elevated position relative to the magnetic modules 12, 14, 16, and 18. The selective positioning of first cooling module 66 and the pressurizable reservoir 72 allows gravity to force cooling fluid into each of the magnetic modules when the system is off. This gravity feed ensures that each of the magnetic modules 12, 14, 16, 18 are supplied with cooling fluid.

Returning to FIG. 2, the magnetic modules 12, 14, 16, and 18 have apertures disposed within them. The aperture 2a is disposed within magnetic module 12, which is selectively, operatively aligned with hole 612, which is not depicted in FIG. 2 but is best shown in FIG. 1. The aperture 2b is selectively disposed within the magnetic module 14, which is selectively and operatively aligned with hole 610, which is not shown in FIG. 2 but is best depicted in FIG. 1. The aperture 2d is selectively disposed within the magnetic module 18, which is selectively, operatively aligned with hole 614, which is not shown in FIG. 2 but is best depicted in FIG. 1. The aperture 2c is selectively disposed within magnetic module 16, which is aligned with hole 616, which is not shown in FIG. 1 but is beat best depicted in FIG. 1.

The magnetic modules 12, 14, 16, and 18 include a ferromagnetic housing 40a, 40b, 40c, and 40d with non-ferromagnetic segments 29a, 29b, 29c, and 29d, which are not show in FIG. 2 but are depicted in FIG. 4, on a side forming apertures 2a, 2b, 2c, and 2d respectively.

Tubular sleeves 30a, 30b, 30c, and 30d are selectively disposed within the apertures 2a, 2b, 2c, and 2d respectively. The tubular sleeve 30a, which is substantially similar to tubular sleeves 30b, 30c, and 30d, is best depicted in FIG. 4. The tubular sleeves 30a, 30b, 30c, and 30d can be made from an insulating material, such as PVC.

The system should always have at least one aperture 2a, 2b, 2c, or 2d adapted to receive an end of a limb of an animal. In a preferred, non-limiting embodiment, the system includes four apertures 2a, 2b, 2c, and 2d adapted to receive a limb of an animal.

Referring now to FIG. 4, magnetic module 12 is depicted, however, it should be understood that each magnetic module 12, 14, 16, and 18 have the same components. Magnetic module 12 has a wound magnetic wire coil 38, which surrounds the aperture 2a.

The wound magnetic wire coil 38 is contained within a ferromagnetic housing 40, which has a non-ferromagnetic segment 29a. The wound magnetic wire coil 38 is operatively positioned upon a perforated spindle 10. The wound magnetic wire coil 38 generates an electromagnetic field. A separate wound magnetic wire coil 38 is located within each magnetic module 12, 14, 16, and 18. Each wound magnetic wire coil located within the magnetic modules 12, 14, 16, and 18 creates an independent electromagnetic field.

FIG. 4 also depicts the end cap 104 which is selectively attached to each tubular sleeve 30a, 30b, 30c, and 30d.

The perforated spindle 10 allows cooling fluid to flow through the wound magnetic wire coil 38 providing continuous cooling.

To help ensure adequate fluid flow to cool the tubular sleeve, spacers 78 and 79 are used to separate the perforated spindle 10 from the non-ferromagnetic segment 29a.

Figure 5:
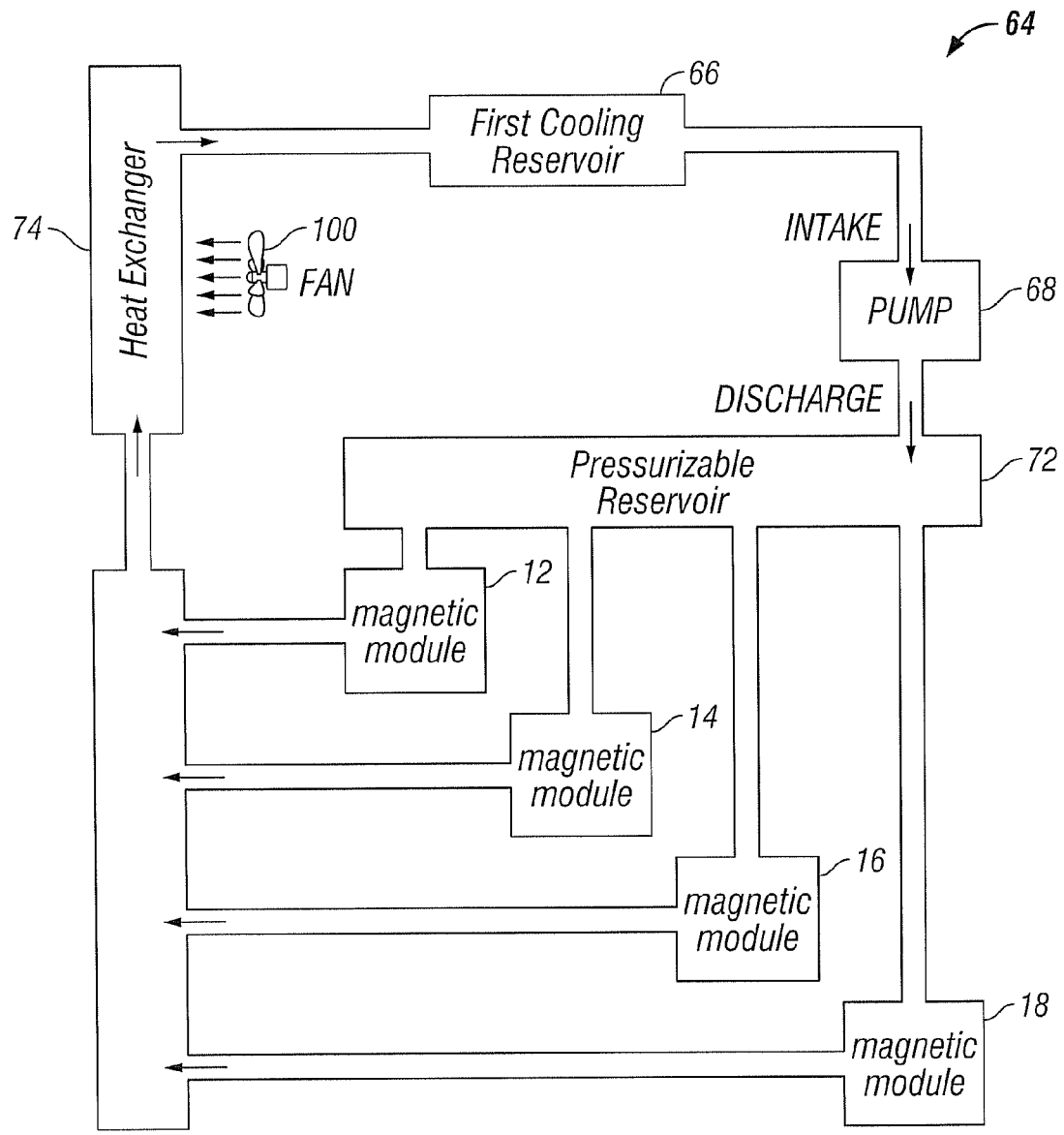
FIG. 5 is a schematic of an embodiment of the continuous flow cooling system.

Referring now to FIG. 5, a schematic of the continuous flow cooling system 64 is depicted. The fluid can flow under the force of gravity or other means from the first cooling reservoir 66 to the presuriazable cooling reservoir 72. The fluid is selectively allowed to reach a homogenous equilibrium temperature within the presurizable cooling reservoir 72. The pump 68 forces the fluid out of the presurizable cooling tank into each module 12, 14, 16, and 18. When the constant amplitude electromagnetic system is not coupled to a power source, gravity can cause fluid to flow into the modules 12, 14, 16, and 18. This ensures that cooling fluid is always in the magnetic modules 12, 14, 16, and 18.

The cooling fluid that flows into each magnetic module 12, 14, 16, and 18 is at a substantially similar temperature. For example, but without limitation, if magnetic module 12 was not supplying a constant amplitude electromagnetic field and magnetic module 16 was supplying a constant amplitude electromagnetic field, an animal having an end of a limb in the magnetic module 12 would not know by the temperature of the magnetic module 12 that magnetic module 12 was not generating a constant amplitude electromagnetic field. The cooling fluid maintains the temperature throughout the magnetic modules 12, 14, 16, and 18 at less than 105 degrees Fahrenheit.

The pump 68 pressurizes the cooling fluid in the presurizable cooling reservoir 72. The pump 68 does not generate more than 20 psi. It is contemplated that the pump 68 can be a switched magnetic coupling fluid circulation pump; however, other pumps that generate small pressures may be used.

FIG. 5 further depicts a heat exchanger 74. The heat exchanger 74 is used to continuously or periodically dissipate heat to the outside environment. It is contemplated that the heat exchanger can be coupled to a heat sink, allowing for both convection and conduction heat transfer.

In another alternative embodiment, the heat exchanger 74 and the pump 68 can be selectively located in a location remote from the housing 600.

Figure 6:
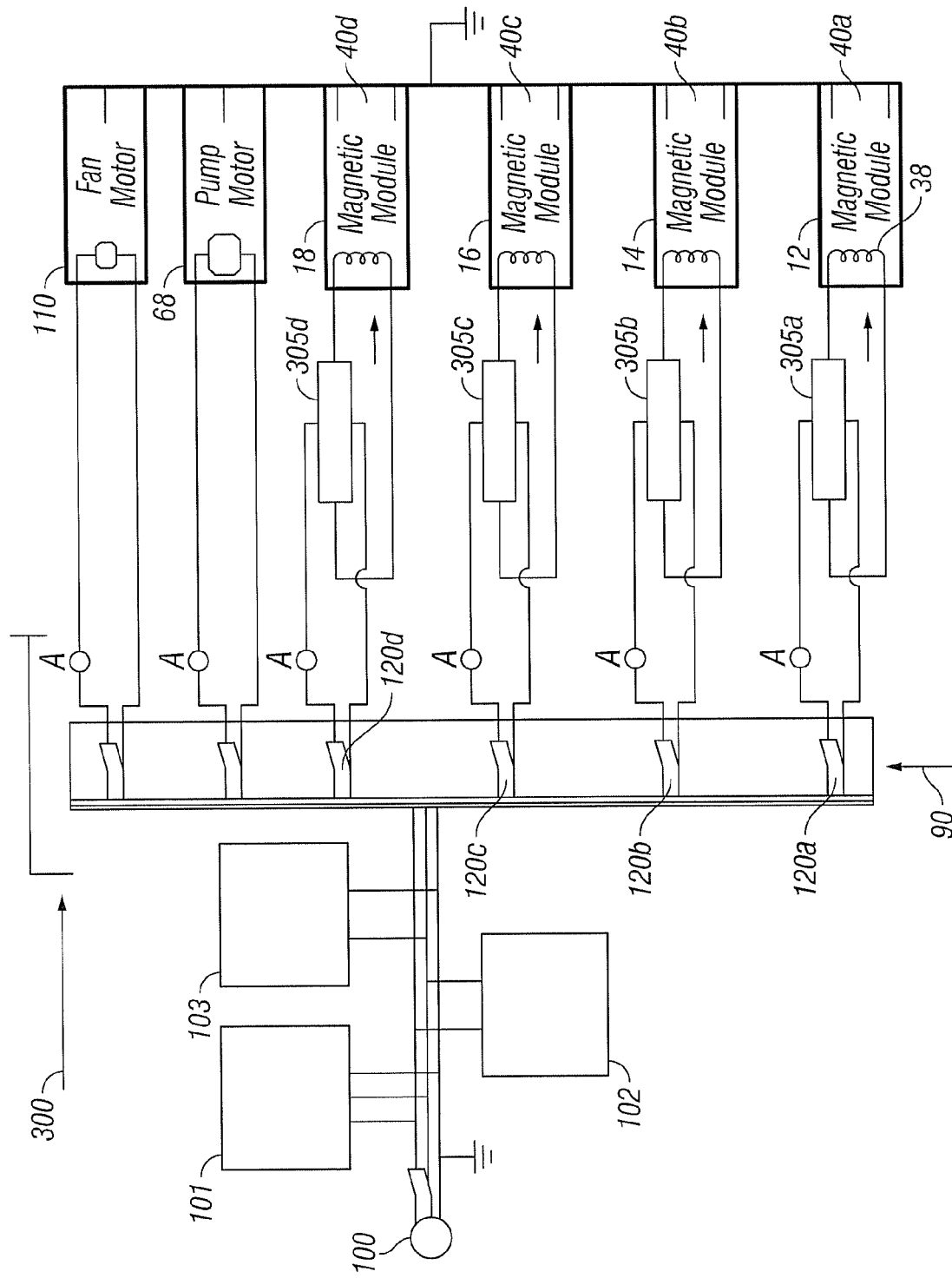
FIG. 6 is an electronic schematic of an embodiment of the electric system.

FIG. 6 is s schematic of an embodiment of the electrical system of the constant amplitude electromagnetic system. A plurality of switches 90 are selectively contained within a control panel 300, which is selectively located upon the housing 600. The plurality of switches 90 are used to couple power to each magnetic module 12, 14, 16, and 18.

Each switch, 120a, 120b, 120c, and 120d within the plurality of switches 90 are independently operated to couple direct current 62 to the separate magnetic modules 12, 14, 16, and 18 respectively.

Other switches can be selectively included within the plurality of switches 90 for controlling other parts of the constant amplitude electromagnetic system, such as the switchable continuous flow cooling system 64.

By the selective operation of the switches 120a, 120b, 120c, and 120d, the magnetic modules 12, 14, 16, and 18 can be operated independent of each other. When the AC power is coupled to the rectifiers 305a, 305b, 305c, 305d by the use of the switches 120a, 120b, 120c, and 120d the AC current is transformed into direct current 62, which is supplied to the wound magnetic coils 38. The direct current 62 can be independently supplied to the wound magnetic wire coils 38 in any of the magnetic modules 12, 14, 16, or 18 by selectively activating one of the switches 102a, 102b, 102c, or 102d respectively. When the direct current 62 is supplied to the wound magnetic coils 38 a constant amplitude electromagnetic field is generated.

The control panel 300, which contains the plurality of switches 90 is selectively located upon the housing 600. Housing 600 is not depicted in FIG. 6.

FIG. 6 further depicts an AC current power input 100. A surge arrestor 101 is located between the AC current power input 100 and the rectifiers 305a, 305b, 305c, 305d. The rectifiers 305a, 305b, 305c, and 305d independently transform the AC current into DC current 62 before the power is supplied to the magnetic modules 12, 14, 16, and 18. Additionally, a power line filter 102 is also disposed between the surge arrestor 101 and the rectifiers 305a, 305b, 305c, 305d. A fail safe circuit 103 is also shown disposed between the power line filter 102 and the rectifiers 305a, 305b, 305c, 305d.

For example, if magnetic module 12 was turned on, AC current would flow from the power input 100 through the surge arrestor 101, past the fail safe circuit 103, through the rectifier 305a, and then to the magnetic module 12. If the fan 110 or pump 68 were turned on simultaneously or independently from the magnetic module 12, the AC current would flow from the power input 100, through the surge arrestor 101, past the fail safe circuit 103, then to the fan 110 or pump 68.

The electromagnetic field is independently generated in each of the modules 12, 14, 16, and 18, which are best depicted in FIG. 2. The electromagnetic field has a closed form and is more spatially confined because of the attraction to the ferromagnetic housing 40a, 40b, 40c, 40d, which are best depicted in FIG. 2. The benefits include preventing interference with external devices, concentrating the field in a desired location, preventing unwanted exposure to other body parts, and providing lower levels of amplitude fields away from the housing.

Figure 7:
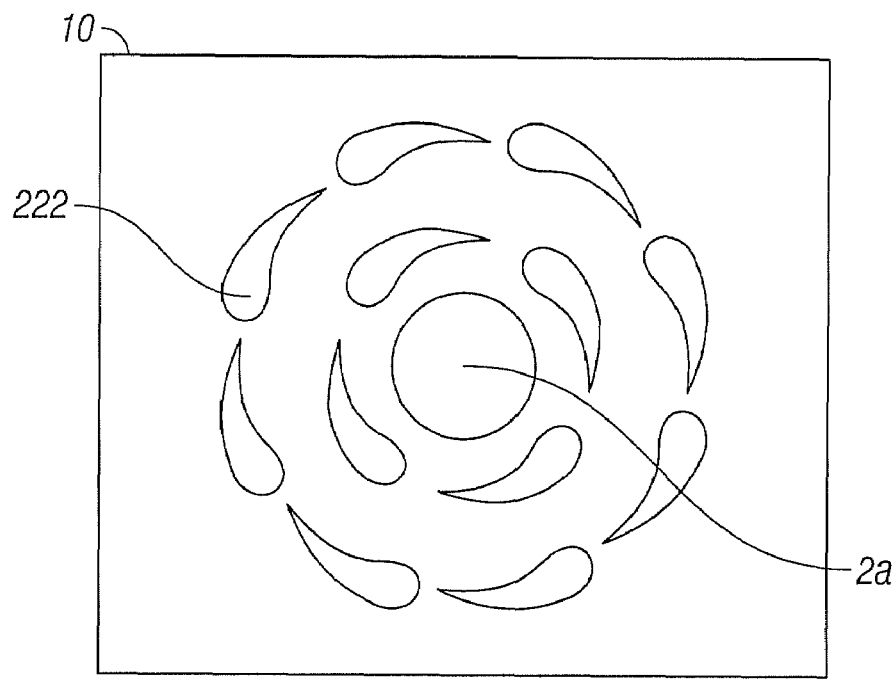
FIG. 7 is a depiction of an embodiment of the perforated spindle.

FIG. 7 is a view of the perforated spindle 10. The perforated spindle 10 has a plurality of elliptical openings 222. The elliptical openings 222 allow the cooling fluid to surround the wound magnetic wire coil 38 more efficiently. The perforated spindle 10 is shown having the aperture 2a, however it should be noted that the perforated spindle 10 is the same in each magnetic module.

The elliptical openings 222 are arranged so that the cooling fluid will flow towards the center of the wound magnetic wire coil 38, not shown in FIG. 7, producing a circular clockwise flow pattern before exiting. As the cooling fluid is exiting the wound magnetic wire coil 38 through the end of the perforated spindle opposite the end of cooling fluid entry, the elliptical openings 222 will cause the fluid to continue to flow towards the center of the wound magnetic wire coil 38.

Figure 8:
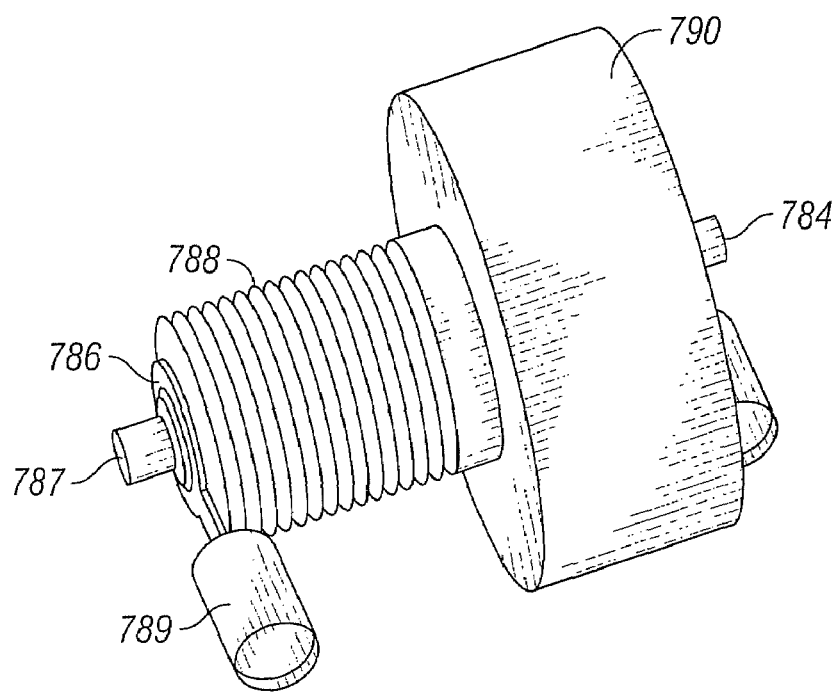
FIG. 8 illustrates a schematic of an embodiment of an electrical connector.

FIG. 8 illustrates an exemplary electrical connector 780 for the housing 600 that reduces fluid leakage from the modules 12, 14, 16, and 18 via the electrical connection. Electrical connector 780 comprises a conductor post 784 that provides an external terminal connection 786 and an internal terminal connection 787 that span the modules 12, 14, 16, and 18 and connect the wound magnetic coil 38 to the wire 789 for transporting the direct current 62. The connector 780 can be attached to the housing 600 by threaded member 788. The connector can be attached using various washer and gasket configurations, which include a gasket or washer positioned between the external connector body 790 and the housing 600.

It is contemplated that an embodiment of the constant amplitude electromagnetic system can be used under medical supervision for adjunctive therapy for the treatment of medical diseases and conditions.

The constant amplitude electromagnetic system of the invention may be indicated for use in stimulating neuromuscular tissues for bulk muscle excitation in the legs or arms for rehabilitative purposes.

Magnetic therapy systems have been used for the relief of pain with demonstrated efficacy and safety. Other similar systems have delivered electromagnetic energy either transcutaneously or invasively for pain relief and to promote healing and bone growth.

Electrical and magnetic nerve stimulation has been used for over a hundred years, but more importantly over the past 20 years, with sound medical studies and supervision. The use has shown well-established positive results in pain relief without negative side effects.

Each stimulation system may have different body responses based on its particular delivery of electromagnetic energy. There exist almost unlimited possible variations in the electromagnetic field through changes in current, voltage, frequency, waveform and length of delivery of the energy.

The constant amplitude electromagnetic system of the present invention delivers electromagnetic energy at very low levels, well within parameters of other FDA approved magnetic stimulator systems. Its purpose and intended use is similar to other stimulator systems: to relieve pain and to possibly affect the electric potential of an unhealthy human blood cell. These systems are intended to be used for the relief of pain which has been determined by adequate medical diagnosis as being chronic or in response to conditions known and being treated.

The body cell functions, being a complicated combination of electrical and chemical ion interactions, may be directly affected by the constant amplitude electromagnetic field.

Alternative embodiments of the system described herein provide delivery of electromagnetic energy in a form which provides many of the same type of cell interactions as other magnetic stimulation systems. The importance of this system is that it provides pain relief, potentially affects greater body volume and in some cases provides a longer lasting treatment effect, at significantly safer electromagnetic levels, with an inherently safer delivery system and a more easily performed procedure.

The electromagnetic system has been tested on people with diabetes. Diabetes is the most common chronic disease in the developed countries, with more than one hundred million cases diagnosed worldwide, and sixteen million diagnosed in the United States. It is the third most common cause of death in the U.S. Approximately one percent of all diabetes patients undergo amputations, a rate fifteen times higher than the non-diabetic population.

An estimated seventy percent of diabetic patients have nerve damage that impairs feeling in their feet. Fifteen percent of all diabetics eventually will develop a foot ulcer. Among those with ulcers, one in four will lose a foot. Every year, over 86,000 amputations are performed as a result of diabetes, and studies show that about one half of those who have a foot or leg amputated will lose the other one within five years.

Blindness and visual disability are caused due to diabetes mellitus. The blood vessels in the retina are damaged due to this chronic autoimmune disease which eventually results in loss of vision. It is possible to suggest from findings, consistent from study to study, that approximately two percent of diabetics become blind after fifteen years of diabetes, while severe visual handicaps are developed by about ten percent of diabetics. Loss of vision from certain types of glaucoma and cataracts may be more common in people with diabetes than in those without it.

The constant amplitude electromagnetic treatment system has been tested, over the span of several years, on thousands of human patients. There has been an ongoing exchange of information regarding the constant amplitude electromagnetic system with the United States Food and Drug Administration (FDA). The FDA has ruled that it is a "non-significant-risk system." No adverse side effects have been noted in the patients treated, and the number of experimental treatments administered exceeds fifteen thousand. The constant amplitude electromagnetic treatment system has been observed to be effective to a significant degree in reducing pain in a wide variety of diseases, injuries, and other medical conditions. Patients with various diabetic complications are among those whose pain scores have been shown to be reduced after treatments.

Type 1 diabetes requires that insulin be replaced directly. Type 2 diabetics have various drugs available to enhance the production of natural insulin rather than replacing it. Various combinations of drugs may be tried as the disease progresses. Eventually, natural insulin may completely fail, requiring insulin replacement.

Tight control of blood glucose levels delays the onset and slows the progression of neuropathy. Certain drugs and even natural supplements have proved helpful. Tight insulin control is needed to help prevent retinopathy. Once damage to the eye develops, surgery may be needed.

Experimental treatment with the constant amplitude electromagnetic treatment system has been demonstrated in previous studies to be an effective treatment modality for reducing the severity of symptoms of both diabetic neuropathy and diabetic retinopathy.

Sickle cell disease is an inherited blood disorder characterized by defective hemoglobin. It affects millions of people throughout the world and approximately 72,000 people in the U.S. It is present in one of every 500 African-American births.

Normal hemoglobin cells are smooth and round, allowing for ease in moving through blood vessels. Sickle cell hemoglobin molecules are stiff and form into the shape of sickle or a scythe. They tend to cluster together and cannot easily move through blood vessels. Clusters may cause a blockages and stop the movement of oxygen-carrying blood. Sickle cells die after about 10 to 20 days, unlike normal hemoglobin cells, which live for up to 120 days. This results in a chronic short supply of red blood cells, which causes anemia. In this condition, most or all of the normal hemoglobin (HbA) has been replaced with the sickle cell hemoglobin (HbS). This is referred to as HbSS. It is the most common and most severe form of the sickle cell variations. These persons suffer from a variety of complications due to the shape and thickness of the sickle cell. Severe and chronic anemia is also a common characteristic for children with HbSS. (www.umm.edu).

Current specific treatment regimens for those who suffer sickle cell anemia are determined by the treating physician according to the patient's age, overall health, and medical history. Other factors include the extent of the disease; tolerance for specific medications, procedures, or therapies; expectations for the course of the disease; and the patient's opinion or preference. Treatments may include pain medications (for sickle cell crises); drinking plenty of water daily (eight to ten glasses) or receiving fluid intravenously (to prevent and treat pain crises); blood transfusions to relieve anemia and to prevent stroke, and to dilute the HbS with normal hemoglobin to treat chronic pain; acute chest syndrome, splenic sequestration, and other emergencies; folic acid (to help prevent severe anemia); hydroxyurea, a medication that helps reduce the frequency of pain crises and acute chest syndrome, and may decrease the need for frequent blood transfusions; bone marrow transplants, which has been successful in curing some persons with sickle cell disease, and/or penicillin (to prevent infections).

The established efficacy of the constant amplitude electromagnetic system to either replace or augment any of the established treatment modalities would be a highly desirable event. Anecdotal evidence suggests a strong possibility of this event being accomplished.

Another contemplated use for the constant amplitude electromagnetic system is treating people affected with Acquired Immune Deficiency syndrome (AIDS). AIDS is an impairment of the body's ability to fight disease. It leaves the affected individual vulnerable to illnesses that a healthy immune system might overcome. AIDS patients are susceptible to diseases called opportunistic infections. These are illnesses caused by organisms commonly found in the environment, that are generally harmful only to an individual with a weakened immune system. This lack of an immune system alters the lives of these patients in important ways. AIDS affects approximately two million people in the United States.

AIDS patients are affected by early symptoms that are usually benign and inconspicuous, and may include fatigue; loss of appetite; fever; night sweats; swollen glands (enlarged lymph nodes) in the neck, armpits, or groin; unexplained weight loss, diarrhea, persistent cough, and various skin lesions. However, the symptoms may persist for months or worsen as opportunistic diseases exploit the body's collapsed defenses. Many (about 52%) develop an unusual pneumonia caused by the protozoan *Pneumucysti carinii*. Another third of patients exhibit a rare cancer of the skin, Kaposi's sarcoma (KS) or contract one of the many opportunistic diseases caused by fungi (yeasts), viruses, bacteria, and protozoans.

AIDS patients may be divided into three groups: (i) AIDS patients having only Kaposi's sarcoma (KS) and no other symptoms, (ii) AIDS patients having only severe opportunistic infections, such as *Pneumucysti carinii* pneumonia (PCP), or *Candida* (thrush), (iii) AIDS patients having both KS and opportunistic infections. The third group suffers the most severe changes in their immune systems, while patients with KS alone are the least severe.

The present treatment of AIDS includes the use of various pharmaceuticals; AL-721, Ampligen, Azidothymidine (AZT), Recombinant soluble CD4 (T4), Dextran sulfate, Dideoxycytidine (ddC), Foscarnet, Interferons, Ribaviron, among others, which are used alone or in combination. One goal of AIDS treatment is the complete suppression of the crisis without the development of collateral effects related to the medicine. Medicinal therapies are not sufficient to control the AIDS crisis. The recurring crisis has a long lasting effect on a patient's cognitive and psychosocial development, as well as on a patient's quality of life.

Recently, magnetic stimulation has been used with success for the treatment of AIDS. Although the mechanism of action remains unknown, the following hypotheses have been postulated: The first is the cancellation of AIDS symptoms is related to the destructive interference of the coherent magnetic wave produced by the stimulation. The second is that the magnetic or electrical properties of the affected cells are changed. A third hypothesis is that the magnetic stimulation produces an inhabitation of the viral activity in the region that produces dysfunction of the immune system. A fourth hypothesis is that the magnetic fields alter the properties at the biologic membranes, regulating a variety of ionic pumps.

Another hypothesis is based on studies that have shown that T4 cells directly or indirectly regulate immune function. Magnetic stimulation suppressed the activity of the endogenous opioid peptides. Some drugs, such as phenotoin, Phenobarbital, and sodium valproate reduce the concentration of beta-endorphins in rats, suggesting that the mechanism of action of these drugs may be partly behind the interaction with the endogenous opioid peptides.

In still further study, the application of magnetic fields has been shown to influence the activity of purkinje cells in the brain, and because it is known these cells participate heavily in the initiation, as well as the propagation of the cerebral activity, it is possible that the effects of magnetic fields can affect cerebral activity. The reduction of AIDS symptoms may be related in part to the disease's interference with cerebral functions. Autopsies reveal signs of neurological disease in 80 percent to 90 percent of people who die from AIDS.

In yet another study, the pineal gland is believed to be a magnetism-sensitive organ. It is conceivable that the effects of magnetic fields upon AIDS may be mediated via pineal gland. It has been demonstrated that magnetic fields affect the pineal glands producing structural changes, reduction of serotonin-N-acetyl tranferase and hydroxyindol-orthomethyl transferase; reduction in the production of melatonin; behavior opposite that which the rat exhibits with the administration of melatonin. All of these discoveries indicate that changes in the magnetic environment can influence the production of melatonin and the modulation of the circadian rhythms dependent on the pineal gland.

The following evidence supports the association between the pineal gland activity and AIDS: (a) melatonin influences the electric activity of the brain in human beings and animals, (b) administration of tritiated melatonin shows an accumulation in the cerebral structures which integrate cerebral activity (i.e., the hippocampus and the cerebellum); (c) the administration of melatonin produces dischronation of the electroencephalogram; (d) the intraperitoneal administration of melatonin in small doses augments the discharge of neurons from the red nucleus; and (e) a pinealectomy produces general paroxysmal crisis of slow waves with high amplitudes of cephalic center organ.

The following examples are included to demonstrate alternative, non-limiting, embodiments of the invention. It should be appreciated by those skilled in the art that the techniques disclosed in the examples which follow represent alternative non-limiting techniques discovered by the inventor to function well in the practice of the invention. However, those skilled in the art should, in light of the present disclosure, appreciate that many changes can be made in the specific embodiments which are disclosed and still obtain a like or similar result without departing from the spirit and scope of the invention.

One example of a use of the constant amplitude electromagnetic system involves a female participant who was suffering from sickle-cell anemia. The participant received three treatments using the constant amplitude electromagnetic system as described herein. Blood was drawn before and after the third treatment. Peripheral smears were evaluated for differential RBC counts.

Pre-treatment sickle-cell percentage was 25% (75% non-sickle cells). Post treatment sickle-cell percentage was 10% (90% non-sickle cells). It is contemplated to expand these studies to greater number of patients to further support these results.

In another example, one patient had epileptic attacks for 28 years, with an occurrence from 1 to 2 times per month, and was selected for treatment by the constant amplitude electromagnetic system described herein. After having been treated by the constant amplitude electromagnetic system for about two months, she substantially improved because at least two thirds of her attacks were relieved.

In a third example, an epileptic woman who had experienced at least 8 attacks per month for 34 years was also exposed to the constant amplitude electromagnetic field, and at the end of a six-week period, she was evaluated. She had only four attacks, which occurred during the first four weeks of the treatment period, while during the last three weeks of the treatment no attacks occurred.

In a fourth example, an epileptic woman who had suffered attacks for the last 9 years was selected for constant amplitude electromagnetic treatment for a period of approximately two months. Prior to her treatment, this patient had convulsive attacks with a frequency of 3 to 12 per month. Her attacks diminished to 7 times during the two month evaluation period, no attacks having occurred the last ten days of the period. The treatment was suspended because she became pregnant.

In a fifth example, a 33 year old epileptic woman, who had from 1 to 3 attacks per month for 15 years, was treated for ten weeks. The patient had only one attack at the beginning of the treatment, and no attacks occurred for the remaining period of constant amplitude electromagnetic treatment.

In a sixth example, a 19 year-old woman, who had from 8 to 20 epileptic attacks per month for 4 years, was treated by the constant amplitude electromagnetic field system, and within the first 5 days this patient had 16 attacks. During the following 10 days, the frequency of the attacks diminished to 4 attacks in this latter period, and during the last 10 days of the evaluation she had only 3 attacks. A significant reduction in the occurrence of the epileptic attacks was noted.

The patients described in examples 2-6 have been treated to control their convulsive attacks by means of anticonvulsive medicine, such as Phenobarbital, phenytoin, valproic acid, primidone, carbamazepine, etc. Except for the third patient, all of the patients remain under treatment by the constant amplitude electromagnetic field system described herein and encouraging results have been obtained for each patient.

In a seventh example, the effectiveness of pain relief using the compositions and methods of the present invention has been documented in patients undergoing treatment using the constant amplitude electromagnetic system and method of providing described herein. An open label study of 79 subjects was made. The secondary effect of pain relief was observed and documented in patients being treated. The results of a study documenting pain relief are presented in the Provisional Application incorporated by reference in its entirety. The effect of the constant amplitude electromagnetic system was measured for pain relief for a wide range of maladies causing pain.

Included in the study were subjects suffering from poor circulation, arthritis, fibromyalgia, multiple sclerosis, back pain, neuropathy, diabetes, and other diseases. For 1,195 painful locations compared before treatment and after treatment, there was an average reduction in pain level after treatment of 2.39 points, on a scale of 0 being no pain and 10 being unbearable pain.

In an eighth example, a contemplated treatment schedule for the treatment of AIDS includes: (a) A double blind study; (b) patients will be selected on the basis of the complete break-down of their immune system, only patients in sever crisis will be used; (c) patients will be numbered in consecutive integers. Patients with an odd number will be treated with the constant amplitude electromagnetic system described herein, with the magnetic modules in an on position (relative to the generation of the constant amplitude electromagnetic field, the switchable continuous flow cooling system will also be activated). Patients with an even number will be treated with the magnetic modules in an off position.

Patient will receive CBC-Diff, SMA-20, and an immune deficiency panel blood test before the initial treatment. Patient will receive a one hour treatment. Patient will, immediately after treatment, be given another CBC-Diff, SMA 20, and an immune deficiency panel blood test. This will be followed for three to five days while the results of the first treatment are tested. The Patient will receive another CBC-Diff, SMA 20, and an immune deficiency panel blood test. Patient will receive the Second Treatment, it will be one hour in duration. Immediately after the second treatment the Patient will receive another CBC-Diff, SMA 20, and an immune deficiency panel blood test. This will be followed by three to five days, while the results are analyzed. Patient will receive another CBC-Diff, SMA 20, and an immune deficiency panel blood test. Patient will receive a third treatment, it will be one hour in duration. Patient will receive another CBC-Diff, SMA 20, and an immune deficiency blood panel blood test. After the results of this test are received, the Patient will receive another CBC-Diff, SMA 20, and an immune deficiency panel blood test. The results of these tests and charts are provided in the Provisional Application, incorporated by reference in its entirety.

In a ninth example, previous studies of a randomized, controlled double-blind design have shown that the constant amplitude electromagnetic system treatment for complications due to diabetes is effective. A further study is contemplated to confirm these findings, and to gain further data on efficacy of treatments. The study should be conducted in a location where a population exists that are inflicted with the disease at a rate higher than that found in some areas of the United States. A principal investigator (PI) will be located in such a location, and the PI will be experienced with extensive treatment of the disease. In addition to measuring subjective severity of symptoms, a blood test to show possible cell separation should be employed. A randomized sham treatment controlled double-blind study design will be used.

The study will be designed to assess clinical symptoms response and blood properties response after the constant amplitude electromagnetic system treatment in patients who have complications due to diabetes mellitus, and to evaluate the safety of the constant amplitude electromagnetic system as a treatment modality.

The primary objectives include: (1) determination of the extent of immediate pain relief as a result of treatment, (2) determination of the progression of pain relief from one interval in the treatment process to the next interval, (3) determination of the changes in blood properties as a result of treatment, (4) determination of the progression of changes in the blood properties from one interval in the treatment process to the next interval, (5) determination of the persistent effect of pain relief two weeks after treatment, (6) determination of the persistent changes in the blood properties two weeks after treatment, (7) determination of the extent of any visual acuity changes immediately after treatment, (8) determination of the progression of any visual acuity changes form one interval in the treatment process to the next interval, (9) determination of the extent of any persistent changes in visual acuity two weeks after treatment, (10) determination of the extent of immediate relief from numbness or tingling from as a result of treatment, (11) determination of the progression of relief from numbness or tingling from one interval in the treatment process to the next interval, and (12) determination of the persistent effect of relief from numbness or tingling two weeks after treatment.

Secondary objectives include: (1) determination of deterioration of comfort levels regarding pain or other symptoms pertinent to diabetes complications diagnoses are noted after treatment, if any, and (2) note any side effects, adverse or otherwise, that may be attributable to the constant amplitude electromagnetic treatment.

This is designed to be a Phase II trial to evaluate safety and to assess the treatment effect on clinical symptoms and blood properties of patients with complications due to diabetes. One hundred patients will comprise the study population. A lesser number may ultimately be used, according to preliminary results experienced. A successful test result will be a net improvement effect for actively treated patients, led the net improvement effect for sham treated patients, of twenty percent (20%) of the patients treated. If 20% of treated patients show improvement in numerical rating scale measurements, or in blood properties, the treatment will be deemed successful.

If preliminary results show that the net treatment effect is that forty percent or more of the patients improve, either numeric rating scale or by blood property changes, and if at least fifteen active-treatment patients have been treated, then the PI at his option, and with the written consent of the sponsor and the RB, may declare the study complete. Or, alternatively, at the PI's option, with written consent of the sponsor and the RB, the study may continue but the requirement for randomized, sham treatment, controlled double-blind methodology will be eliminated. In the event that this study continues on an open-label basis, any number less than one hundred patients that the PI, with the consent of the sponsor and IRB, believes to be adequate for achieving the primary and secondary objectivism will be the agreed number to complete the requirements of this study protocol. If the PI determines that the results are good enough to warrant discontinuing randomized sham double-blind treatments, then he should honor his therapeutic obligation by continuing the study to its logical conclusi0on by treating patients on an open label basis.

The research will follow a randomized sham-treatment controlled double-blind design. A randomization assistant, who will be disinterested third party, and the machine operator will know the treatment control status, but subjects and other personnel will not. The system has a similar noise level and temperature whether in actual or placebo treatment mode, and controls for mode selection will not be visible to participant.

All accepted study participants, whether actually treated or placebo treated, will follow the flowing procedure. (1) Describe the intensity of pain, attributable to complications due to diabetes, experienced just prior to treatment with the constant amplitude electromagnetic system. Locations of pain and related intensity levels will be narrowly defined, such as which fingers or toes are in pain. The NIH numeric rating scale shall be used to define pain levels, (2) determine the intensity of numbness or tingling, attributable to complications associated with diabetes, experienced just prior to treatment of with the constant amplitude electromagnetic system. Location of numbness or tingling and related intensity levels will be narrowly defined, such as which fingers or toes are experiencing the numbness or tingling. The NIH numeric pain scale will be used, (3) read on eye chart to the smallest possible prior to the constant amplitude electromagnetic treatment. A "Bailey Love Chart #4, National Vision Institute of Australia, copyright 1978" or equivalent will be used; (4) have blood drawn sufficient for a CBC test, and peripheral smear prior to constant amplitude electromagnetic treatment, repeat all measurements ands blood sampling described in steps 1 through 4 above, (7) two weeks after treatment by the constant amplitude electromagnetic system, the patient will come back to the treatment site. He or she will repeat all the measurements and blood sampling described in steps 1 through 4 above.

At the follow-up visit two weeks after treatment using the constant amplitude electromagnetic system, the patient will be asked to submit an opinion as to whether he or she received an active or sham treatment. After the measurements and blood sampling is completed according to steps outlined above, the subject patient will be informed as to whether he or she was an active or sham-treated patient. For those active-treated patients their participation in the study will terminate at that time. For those sham-treated subject patients, an offer will be tendered, and encouraged, to participate further with an open label treatment with the constant amplitude electromagnetic system. If the patient agrees to further treatment, the information measured and blood sampling described above will be followed. Their participation in the study will then be concluded.

Each patient will be given a form after their original treatment, for them to list any antibiotics or blood transfusions that they may have received during the two weeks interval between treatment with the constant amplitude electromagnetic system and the follow-up visit. The PI will use that information as pestilential confounding factors in his assessing the efficacy of the constant amplitude electromagnetic system treatment.

The study population is male or female patients, ages 18-80, who meet eligibility requirements. Patients from all races or ethnic groups are invited to participate.

The following conditions must be met before a patient may be enrolled in this study. First, patients must be 18-80 years old. Ages below 18 or above 80 are acceptable with specific approval of the PI. Second, medical records adequate to document that patients have type 1 or type 2 diabetes, with acute pain, chronic pain, mixed pain, acute numbness, or chronic numbness, Third, if patients are experiencing no pain or numbness at time of treatment, objective blood test information, the Fasting Plasmas Glucose Test at the minimum, must be in file to reasonably document and predict prescience of diabetes. Finally, written informed consent conforming with to IRB guidelines must be given.

Any of the following conditions eliminates a patient from participating in this testing. (1) Inadequate records to establish proof of having been diagnosed with diabetes, (2) pregnant or breast feeding, (3) blood transfusions within thirty days prior to treatment with the constant amplitude electromagnetic system, (4) received antibiotic treatment within 14 days prior to treatment with the constant amplitude electromagnetic system, (5) Contraindication to MRI, (6) prior experience with the constant amplitude electromagnetic system, (7) unwillingness or inability to conform to all the steps required to complete the study.

At the time the informed consent is obtained, qualified patients will be assigned a study number.

Patient evaluations will be directed toward the acquisition of data addressing the primary and secondary objectives of the study.

Primary objective—The numeric pain rating scores of each patient will be analyzed to measure the immediate effect of the treatment using the constant amplitude electromagnetic system. Both pain and numbness criteria will be considered. The differential between the scores prior to treatment, after fifteen minutes of treatment, and after thirty minutes of treatment will be computed. A determination of whether the more significant change, if any, occurs in the first fifteen minutes of treatment is of great interest, Then the persistent effect of the pain and numbness scores will be analyzed after two weeks from the treatment date, as compared to scores taken immediately prior to the constant amplitude electromagnetic system treatment., to better evaluate the efficacy of the treatment with the constant amplitude electromagnetic system.

The changes will finally be expressed as a mean change in the scores for the actual treatment cohort and the sham- treatment-control cohort, and compared the differenced between the two. Each participant's perception of his or her being actually treated or sham treated will be compared with the results measured. A reliable indicator, even based as it is on subjective information, of the constant amplitude electromagnetic system's ability to mitigate pain and numbness will be established.

The CBC test and peripheral smear will provide more objective data to determine treatment efficacy. It is contemplated that clustered cells, if any, will separate from each other to some extent even after the first fifteen minutes of treatment. The peripheral smear, with ensuing photographs of it, will test and document this affect. Similarly, it is anticipated that after the fill thirty minutes of treatment, further separation will occur. Correlation to subjective numerical pain and numbness ratings will be made. It is expected that at the two-week follow-up that the smears will show possibly more cell separation.

An attempt will be made to correlate changes in CBC test results with changes in numerical pain and numbness ratings.

Secondary Objectives—All side effects will be noted and their relationships to the treatment process will be examined.

Safety Considerations—Constant amplitude electromagnetic field exposure from the constant amplitude electromagnetic system is much less than that with a MRI. No precautions are required to shield patients or staff from the electromagnetic field exposure, as the measured field strength dissipated to almost zero within approximately six inches from the magnetic modules. Despite the fact of considerably less electromagnetic field strength than a MRI, any patient contraindicated for MRI will not be allowed for treatment.

Adverse Experiences—All adverse experiences (AE) must be recorded and reported. The PI must also notify the RB. The sponsor will maintain records, and will include accounts of AEs, if pertinent, in future filings with the FDA.

Institutional Review—Prior to implementation of this study, the research protocol and the proposed patient consent form must be reviewed by a properly constituted Institutional Review Board. A signed and dated statement that they have approved the protocol must be submitted to the sponsor prior to the start of the study. This IRB must also approve all amendments to the protocol.

Informed Consent—Written consent will be obtained from each patent prior to entering the trial and will become part of the patient's permanent study record. Each patient will be assured that study participation id voluntary and that he/she may withdraw at any time, without penalty.

At the time of obtaining written consent, the investigator will advise patients of the experimental nature of the constant amplitude electromagnetic system, the duration of the trial, alternate modes of treatment, and prevalent adverse reactions that might occur. The patient's signature is to be witnessed.

Reporting and Recording of Data—All information required by the treatment protocol is to be provided, or an explanation given for omissions. All data and information will be typed or legibly printed in black ink for ease of duplication interpretation and analysis.

Although the description of the preferred embodiment has been presented, it is contemplated that various changes could be made without deviating form the spirit of the present invention.

What is claimed is:

1. A method for treating an animal using a constant amplitude electromagnetic field comprising:
    providing at least one constant amplitude electromagnetic field concentrated at a center location by using a wound magnetic wire coil;
    continuously maintaining a substantially similar temperature around each of the areas of each of the at least one constant amplitude electromagnetic fields;
    placing an end of a limb of an animal at the center location;
    exposing the end of the limb of the animal to the constant amplitude electromagnetic field for a length of time ranging from 10 minutes to 3 hours to simultaneously treat venous and arterial blood cells and nerve endings in the limb of the animal; and
    maintaining a temperature at the center location which is less than 105 degrees Fahrenheit that is comfortable for the animal while maintaining a 10 to 15 degrees Fahrenheit temperature gradient between a temperature around the end of the limb and a temperature around the wound magnetic wire coil.

2. The method of claim 1, wherein the constant amplitude electromagnetic field has an intensity ranging from 50 to 1000 gauss at the center location that declines by up to 80% as the distance from the center location increases to 2 feet.

3. The method of claim 1, wherein the limb is a non-damaged limb of an injured animal for treatment of venous and arterial blood cells and nerve endings.

4. The method of claim 1, wherein the end of the limb of an animal is consistently positioned at a repeatable position within the center location.

5. The method of claim 4, further comprising the act of safely preventing the end of the limb of the animal from being away from the repeatable position within the center location.

6. The method of claim 1, wherein the animal is a human.

7. The method of claim 1, further comprising automatically stopping the constant amplitude electromagnetic field when the temperature at the area around the constant amplitude electromagnetic field exceeds a pre-set limit.

8. The method of claim 1, further comprising providing from 2 to 4 constant amplitude electromagnetic fields, wherein the constant amplitude electromagnetic fields are adapted to treat an end of a limb of an animal.

9. The method of claim 8, further comprising continuously cooling the area around the constant amplitude electromagnetic fields simultaneously, wherein the continuous cooling comprises a flowing of cooling fluid to a pressurizable reservoir for providing pressurized cooling fluid to the wound magnetic wire coil.

10. The method of claim 9, further comprising maintaining substantially similar temperatures between each of the constant amplitude electromagnetic fields.

11. The method of claim 8, wherein each constant amplitude electromagnetic field is provided independent of other constant amplitude electromagnetic fields.

12. The method of claim 1, wherein the continuous maintaining of the substantially similar temperature is done with a cooling fluid.

13. The method of claim 12, wherein the cooling fluid is hydrotreated light naphthenic petroleum oil.

14. The method of claim 1, further comprising supplying a direct electric current to generate the constant amplitude electromagnetic field.

15. The method of claim 1, further comprising providing from 2 to 4 constant amplitude electromagnetic fields wherein each constant amplitude electromagnetic field is adapted to treat the ends of limbs of different animals simultaneously.

16. The method of claim 15, further comprising continuously cooling the area around the constant amplitude electromagnetic fields simultaneously, wherein the continuous cooling comprises flowing cooling fluid to a pressurizable reservoir for providing pressurized cooling fluid to the constant amplitude electromagnetic fields.

17. The method of claim 16, wherein the cooling fluid is hydrotreated light naphthenic petroleum oil.

18. The method of claim 16, further comprising maintaining substantially similar temperatures between each of the constant amplitude electromagnetic fields.

19. The method of claim 16, further comprising periodically removing heat from the cooling fluid to an external environment.

20. The method of claim 16, further comprising supplying a direct current to generate the constant amplitude electromagnetic field.

* * * * *